(12) United States Patent
Chenal

(10) Patent No.: US 10,940,043 B2
(45) Date of Patent: *Mar. 9, 2021

(54) SOUND ATTENUATION APPARATUS AND METHOD

(71) Applicant: JMJ Holdings, LLC, Frederic, WI (US)

(72) Inventor: David M. Chenal, Frederic, WI (US)

(73) Assignee: JMJ Holdings, LLC, Frederic, WI (US)

( * ) Notice: Subject to any disclaimer, the term of this patent is extended or adjusted under 35 U.S.C. 154(b) by 322 days.

This patent is subject to a terminal disclaimer.

(21) Appl. No.: 15/566,699

(22) PCT Filed: Apr. 15, 2016

(86) PCT No.: PCT/US2016/027820
§ 371 (c)(1),
(2) Date: Oct. 14, 2017

(87) PCT Pub. No.: WO2016/168645
PCT Pub. Date: Oct. 20, 2016

(65) Prior Publication Data
US 2018/0133061 A1 May 17, 2018

Related U.S. Application Data

(60) Provisional application No. 62/148,237, filed on Apr. 16, 2015.

(51) Int. Cl.
*A61F 11/08* (2006.01)

(52) U.S. Cl.
CPC ......... *A61F 11/08* (2013.01); *A61F 2011/085* (2013.01); *A61F 2230/0093* (2013.01);
(Continued)

(58) Field of Classification Search
CPC ...... A61F 11/08; A61F 11/10; A61F 2011/85; A61F 2250/0019; A61F 2250/0039;
(Continued)

(56) References Cited

U.S. PATENT DOCUMENTS 3,783,864 A * 1/1974 Moller ................. H04R 25/656
128/864
5,631,965 A 5/1997 Chang
(Continued)

FOREIGN PATENT DOCUMENTS

DE 4217043 A1 11/1992
ES 2 028 711 A6 * 3/1991
(Continued)

OTHER PUBLICATIONS

English Translation of ES 2 028711 A6.*
(Continued)

*Primary Examiner* — Ophelia A Hawthorne
*Assistant Examiner* — Camtu T Nguyen
(74) *Attorney, Agent, or Firm* — Charles A. Lemaire; Jonathan M. Rixen; Lemaire Patent Law Firm, P.L.L.C.

(57) ABSTRACT

A sound attenuation system can include a first end that can include a shaft and a flange, the flange can be coupled to the shaft, and a second end that can include a filter stem and a cap. The filter stem can have a hole. The cap can have a first position in which the cap occludes the hole and can have a second position in which the cap is clear of the hole.

24 Claims, 6 Drawing Sheets

(52) U.S. Cl.
CPC ............... *A61F 2250/0019* (2013.01); *A61F 2250/0039* (2013.01)

(58) Field of Classification Search
CPC .. A61F 2230/0093; A61F 11/06; A61F 11/00; H04R 1/1016; H04R 1/10
USPC ........... 128/864, 866–867; 181/135; 381/380
See application file for complete search history.

(56) References Cited

U.S. PATENT DOCUMENTS

| | | | |
|---|---|---|---|
| 5,957,136 A | 9/1999 | Magidson | |
| 6,148,821 A * | 11/2000 | Falco | A61F 11/08 128/864 |
| 6,938,622 B2 | 9/2005 | Huang | |
| D523,845 S | 6/2006 | Smith et al. | |
| 7,394,910 B2 | 7/2008 | Smith et al. | |
| 7,512,243 B2 | 3/2009 | Haussmann | |
| 7,600,604 B2 | 10/2009 | Babcock et al. | |
| 7,778,435 B2 | 8/2010 | Smith et al. | |
| 7,837,005 B2 | 11/2010 | Killion | |
| 7,934,916 B2 | 5/2011 | Smith et al. | |
| 8,161,975 B2 | 4/2012 | Turdjian | |
| 8,224,005 B2 | 7/2012 | Smith | |
| 8,611,969 B2 | 12/2013 | Smith et al. | |
| 8,625,834 B2 | 1/2014 | Smith et al. | |
| 8,679,607 B2 | 3/2014 | Hamer et al. | |
| 8,820,470 B2 | 9/2014 | Brown | |
| 8,879,769 B2 | 11/2014 | Smith et al. | |
| D727,301 S | 4/2015 | Smith et al. | |
| 9,042,947 B2 | 5/2015 | Smith et al. | |
| 9,088,847 B2 | 7/2015 | Young-Mun | |
| D771,599 S | 11/2016 | Kim | |
| 9,603,746 B2 * | 3/2017 | Chenal | A61F 11/08 |
| 9,814,625 B2 | 11/2017 | Ely | |
| D815,619 S | 4/2018 | Moudgill et al. | |
| D819,594 S | 6/2018 | Hosoda et al. | |
| 10,231,048 B2 | 3/2019 | Smith et al. | |
| 2002/0096391 A1 | 7/2002 | Smith et al. | |
| 2002/0181729 A1 | 12/2002 | Smith | |
| 2003/0116165 A1 | 6/2003 | Huang | |
| 2003/0159878 A1 | 8/2003 | Hakansson et al. | |
| 2005/0008180 A1 | 1/2005 | Smith et al. | |
| 2008/0181441 A1 | 7/2008 | Smith | |
| 2008/0187161 A1 * | 8/2008 | Tiemens | H04R 1/1016 381/380 |
| 2008/0245372 A1 | 10/2008 | Smith | |
| 2008/0247561 A1 | 10/2008 | Smith | |
| 2008/0253605 A1 | 10/2008 | Smith | |
| 2009/0141923 A1 | 6/2009 | Smith | |
| 2012/0057739 A1 | 3/2012 | Smith et al. | |
| 2014/0014121 A1 * | 1/2014 | Endle | B29C 44/04 128/867 |
| 2014/0105442 A1 | 4/2014 | Smith et al. | |
| 2014/0190494 A1 | 7/2014 | Ely | |
| 2014/0254842 A1 | 9/2014 | Smith et al. | |
| 2015/0043767 A1 | 2/2015 | Smith | |
| 2015/0047651 A1 | 2/2015 | Haapapuro et al. | |
| 2020/0252711 A1 | 8/2020 | Smith et al. | |

FOREIGN PATENT DOCUMENTS

| | | |
|---|---|---|
| ES | 2 028711 A6 * | 3/1991 |
| GB | 2407274 A | 4/2005 |

OTHER PUBLICATIONS

"EPO Search Report/Opinion for related EP Application 16780867. 4, dated Feb. 12, 2019, 8 pages."

Surefire, LLC, Fountain Valley, California, "EP8 Sonic Defenders", "downloaded from: https://web.archive.org/web/20130524145837/ http://www.surefire.com/ep8-sonic-defenders-cobalt.html", May 24, 2013.

* cited by examiner

SOUND ATTENUATION APPARATUS AND METHOD

CROSS-REFERENCE TO RELATED APPLICATIONS, AND CLAIM OF PRIORITY

This patent application is a national-phase filing of, and claims priority benefit of, PCT Patent Application No. PCT/US2016/027820, filed Apr. 15, 2016 by David M. Chenal and titled "Sound attenuation," which claims the benefit of priority of U.S. Provisional Patent Application Ser. No. 62/148,237, filed on Apr. 16, 2015, each of which is hereby incorporated by reference herein in its entirety. This application is also related to U.S. Pat. No. 9,603,746 which issued Mar. 28, 2017 to David M. Chenal, titled "Sound attenuation."

BACKGROUND

An earplug may be inserted into an ear canal of a user to attenuate sound. An earplug user may desire a particular earplug feature, such as a comfortable configuration, ease of insertion or removal from the ear canal, or an ear canal conforming feature. The earplug may be used in various environments where sound may be undesired or harmful to the auditory health of the user, such as military, music or concerts, industrial, or construction environments. Current techniques are inadequate for retaining the earplug in the ear canal. U.S. Pat. No. 8,161,975 refers to a dual mode impulse noise protecting earplug.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
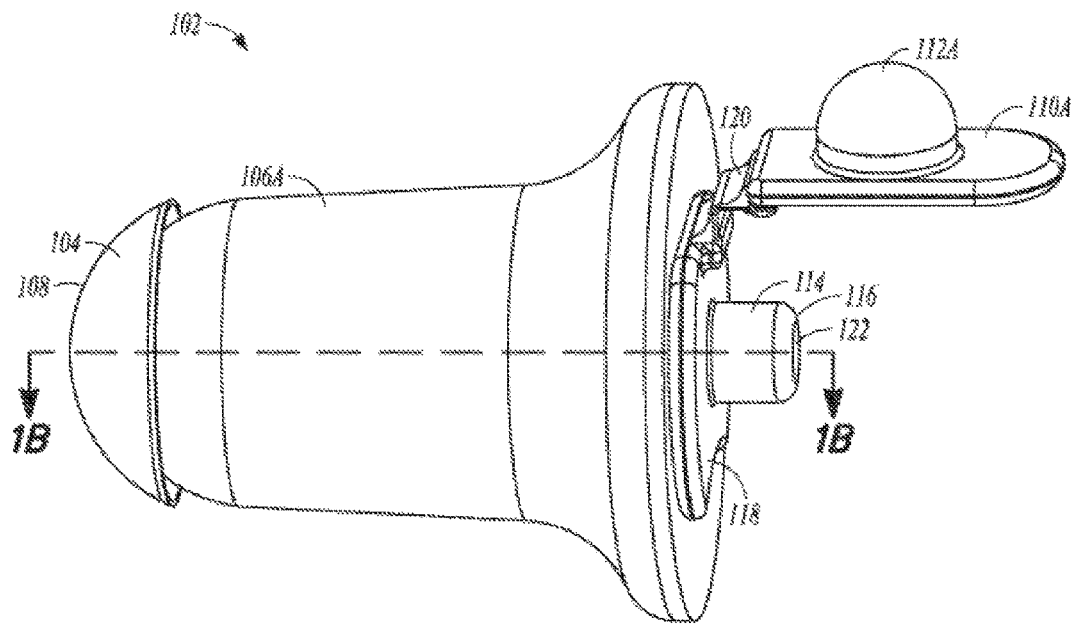
FIG. 1A includes a view of an example of an earplug.

FIG. 1A includes a view of an example of an earplug 102. The earplug 102 includes a first end 108 and a second end 116. The earplug 102 includes a flange 104, a foam body 106A, a cap 110A, a knob 112A, a port boss 114, a base plate 118, a joint 120, and a hole 122. The knob 112A is coupled to the cap 110A. The knob 112A helps the user to grasp the earplug 102.

Figure 1B:
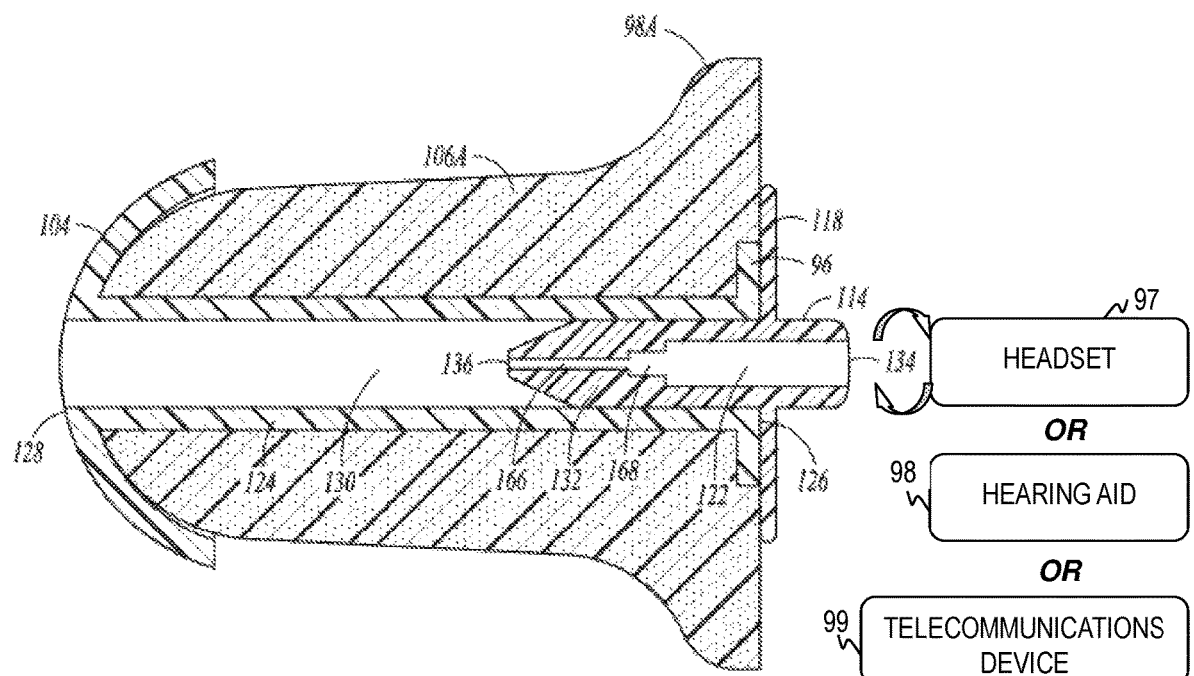
FIG. 1B includes a cross-section view of an example of an earplug.

FIG. 1B includes a cross-section view of a portion of an example of the earplug 102. The earplug 102 includes a tube (e.g., a shaft 124 having a bore 130). The shaft 124 includes a receiver end 126 and an emitter end 128. The bore 130 terminates at the receiver end 126 and at the emitter end 128. The flange 104 is coupled to the shaft 124.

The earplug 102 includes a sound filter, a portion of which is illustrated in the figure. The sound filter includes a filter stem 132. The filter stem 132 includes an inlet end 134 and an outlet end 136. The filter stem 132 includes the hole 122. The hole 122 terminates at the inlet end 134 and at the outlet end 136. The hole 122 extends through the port boss 114. The hole 122 includes a first chamber 166 having a first diameter and a second chamber 168 having a second diameter. In the example of FIG. 1B, the first diameter is less than the second diameter. The filter stem 132 is configured to be at least partially inside of the bore 130. The outlet end 136 is configured to be inside the bore 130. In an example, the filter stem 132 has a press fit with the bore 130, such that filter stem 132 can expand the bore 130. As such, the press fit can use friction to secure the filter stem 132 in the bore 130. A portion of the filter stem 132 is tapered, such as at the outlet end 136 as shown in the example of FIG. 1B. The taper at the outlet end 136 can aid the insertion of the filter stem 132 into the bore 130 in the assembly of the earplug 102. The foam body 106A abuts the base plate 118.

In some examples, the first chamber 166 and second chamber 168 can be positioned, sized, or shaped in different configurations within the hole 122. The first diameter can be greater than the second diameter. The hole 122 can include one or more chambers (e.g., one, two, three, four, or more).

The shaft 124 has a first elastic material. The first elastic material has a first durometer. In one example, shaft 124 includes silicone. The filter stem 132 has a second elastic material. The second elastic material has a second durometer. The first durometer is less than the second durometer. A shape of the ear canal can be non-uniform along its length. The shaft 124 can bend when inserted into the ear canal. The first durometer is configured to allow the shaft 124 to conform to the shape of the ear canal. The present techniques can reduce pressure exerted on the ear canal by the earplug 102. This is because the first material conforms to the ear canal's shape, rather than a more rigid material such as the second material. The second durometer is configured to have the filter stem 132 substantially retain its shape (e.g., the filter stem 132 is more rigid than the shaft 124). In one example, the base plate 118 has the second durometer.

In one example, shaft 124 has a durometer of between 30 and 40 on the shore A scale. In one example, shaft 124 has a durometer of 35 on the shore A scale.

The earplug 102 is inserted into an ear canal of a user to attenuate sound. The user holds the cap 110A of the earplug 102 for inserting the first end 108 into the ear canal. In an example, the user can hold the cap 110A between a finger and thumb. The finger can engage the knob 112A. The thumb can cover the cavity 138. A portion of the thumb can occlude the hole 122 during the insertion of the earplug 102 into the ear canal. In an example, the user presses the thumb onto a portion of the port boss 114 to occlude the hole 122. With the thumb occluding the hole 122, the user can hear that the earplug 102 is positioned at a location that attenuates sound.

In some examples, the knob 112A has various shapes and sizes. The knob 112A is rounded, such as a hemisphere in the example of FIG. 1A. The knob 112A is a cylinder or a box according to some examples. The knob 112A can include multiple units, such as multiple bumps on a surface of the cap 110A configured to help the user grasp the earplug 102. Knob 112A can provide tactile feedback to aid the user in gripping and positioning earplug 102. In one example, knob 112A can provide audible feedback to aid the user positioning earplug 102 with the ear canal. A soft 'pop' can be felt and heard when the knob 112A is moved into a position to occlude the port boss.

In some examples, the knob 112A is optional. In various examples, an elbow component or interface device can engage with the port boss 114, with filter stem 132, or with bore 130 to allow attachment of a headset 97, a hearing aid 98, an interruptible foldback (IFB) device, or a telecommunications device 99.

The base plate 118 is configured to maintain a position of the foam body 106A along the length of the shaft 124. The filter stem 132 is positioned inside the bore 130, such that the receiver end 126 is configured to abut the base plate 118.

Flange 98A, in the example shown in FIG. 1B, has a radius on an inner edge. The outer edge is squared and, in some examples, provides a feature that can engage a prominence on the inner side of the ear anatomy and facilitate device retention. In some users, flange 98A engages the tragus or other anatomic feature. In some configurations, flange 98A is fabricated of a material to mitigate or eliminate abrasion of skin surfaces proximate the foam body. Flange 98A can have a thin cross-section that is configured to deflect under a small force.

In one example, flange 96 is provided at an end of shaft 124. Flange 96 can facilitate retention of foam body 106A on shaft 124 or otherwise limit relative movement, in an axial direction, as to foam body 106A and shaft 124. In one example, flange 96 can be configured to provide a friction fit to retain a filter stem 132 or retain a headset 97, hearing aid 98, IFB, or telecommunications device 99. Flange 96 can take the form of a ring or a raised feature.

Figure 2A:
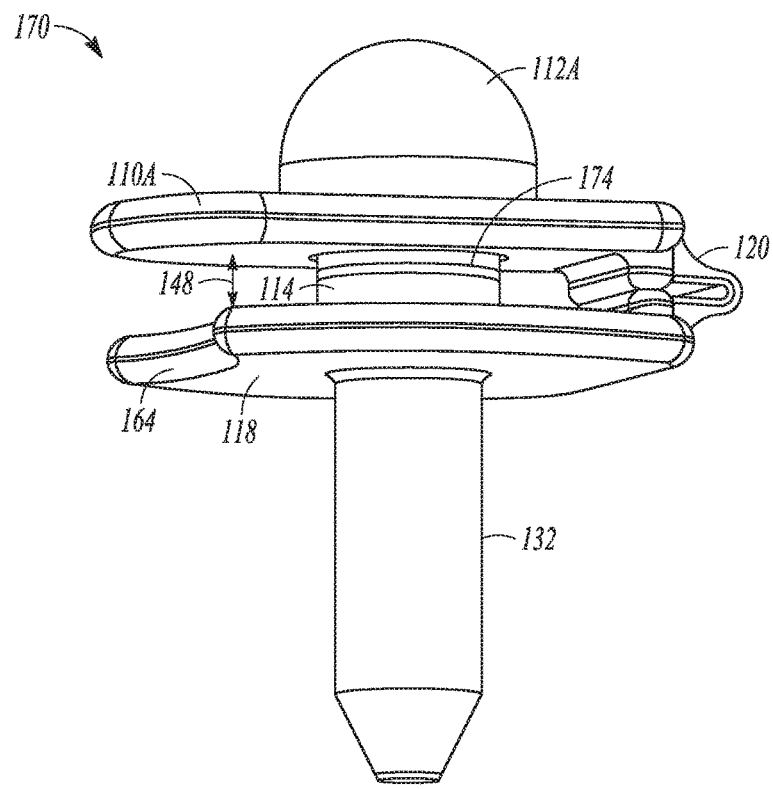
FIG. 2A includes a view of an example of a sound filter.

FIG. 2A includes a view of an example of the sound filter 170. The cap 110A can be in one or more positions. The cap 110A can be in a first position, as shown in FIG. 2A, such that the cap 110A occludes the hole 122 (not visible in this view). The filter stem 132 is coupled to the base plate 118. The cap 110A is coupled to the base plate 118 by the joint 120. The cap 110A can be moved from the first position, such as by the user lifting the cap 110A. The joint 120 can include one or more components. In an example, the joint 120 is movable, and can be described as a hinge configured to allow the cap 110A to be in the one or more positions.

In an example, the joint 120 is a living hinge. The living hinge can have the same material as two rigid members it connects.

In the first position, a gap 148 is between the base plate 118 and the cap 110A. A height of the gap 148 is the axial distance between the base plate 118 and the cap 110A, as shown in FIG. 2A. The gap 148 is configured to aid the user in moving the cap 110A from the first position. The height is configured such that a finger or fingernail can engage and separate the cap 110A from the port boss 114. The base plate 118 includes a notch 164. The notch 164 is configured to aid the user in moving the cap 110A, such as to allow easier access for a user's thumb or finger. The gap 148 and the notch 164 can each aid the user in moving the cap 110A individually or jointly. The port boss 114 is positioned at the inlet end 134 (not visible in this view), such that the port boss 114 includes a portion of the hole 122. In an example, the port boss 114 includes a ring 174. The ring 174 can be raised on the port boss 114 or recessed into the port boss 114.

Figure 2B:
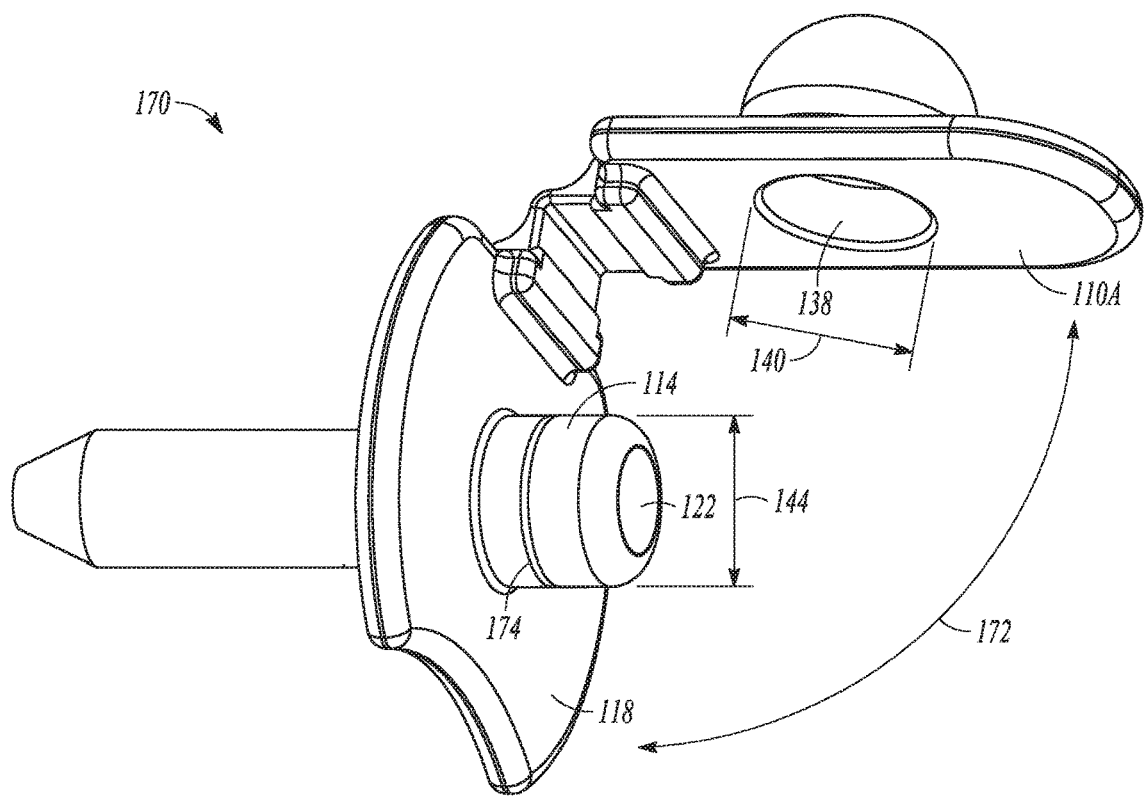
FIG. 2B includes a view of an example of a sound filter.

FIG. 2B includes a view of an example of the sound filter 170. The cap 110A can be in a second position, as shown in FIG. 2B, such that the cap 110A is clear of the hole 122. The cap 110A includes a cavity 138. The cavity 138 has a cavity diameter 140. The port boss 114 has an outer diameter 144. The cavity diameter 140 corresponds to the outer diameter 144. In the second position, there is a space 172 between the base plate 118 and the cap 110A. The space 172 can allow the user to grasp the cap 110A.

Outer diameter 144 and port boss 114 can provide an interference fit aid in retention of cap 110A in an occluded position. In one example, ring 174 can provide an interference fit with cap 110A.

In an example, in the first position, an angle between the base plate 118 and the cap 110A can be 0 degrees (e.g., the base plate 118 is parallel to the cap 110A). The angle can be along the space 172, such as shown in FIG. 2B. In an example, the first position can include an angle greater than 0 degrees, such that the cap 110A occludes the hole 122. In an example of the second position, the angle between the base plate 118 and the cap 110A can range from greater than zero degrees to 180 degrees or more, such that the cap 110A is clear of the hole 122. In an example, when the angle is 90 degrees, the cap 110A is perpendicular to the base plate 118. The position of the cap 110A can be moved along the space 172.

The space 172 of the second position can be configured to allow an attachment to couple to the port boss 114. The attachment can be a speaker, a transducer, tubing, or another unit. The ring 174 can aid in coupling (e.g., securing) the attachment to the port boss 114.

In the first position (e.g., FIG. 2A), the knob 112A is configured to aid in attenuating sound. In an example, a thickness of the knob 112A is configured to increase sound blockage into the hole 122. The knob 112A is coupled to the cap 110A, such that the knob 112A is an external feature of the cap 110A, and the cavity 138 is an internal feature of the cap 110A. The port boss 114 is configured to be at least partially inside the cavity 138 when the cap 110A is in the first position as shown in FIG. 2A. The user can move the cap 110A from the first to the second position while the earplug 102 remains in the ear canal, such as to engage in conversation. Likewise, the user can move the cap 110A from the second to the first position while the earplug 102 is in the ear canal, such as to block high intensity sound.

In some examples, the sound filter 170 can be coupled with a variety of other units to attenuate sound. Such units can include an attachment as described above, or a different type of tube or earplug.

Figure 3A:
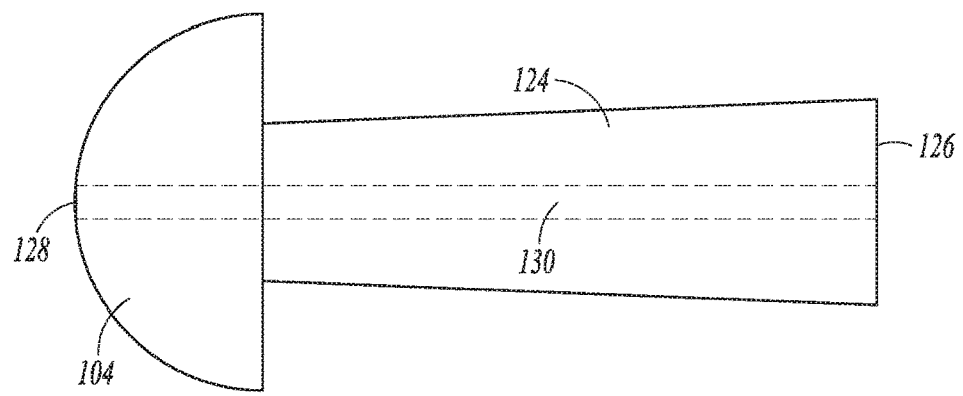
FIG. 3A includes a view of an example of a portion of an earplug.

FIG. 3A includes a view of an example of a portion of the earplug 102. The shaft 124 is coupled to the flange 104. In one example, the flange 104 is positioned at the emitter end 128. The bore 130 extends through a center of the shaft 124, as shown in FIG. 3A. In the example shown, the shaft 124 is tapered. The outer diameter of the shaft 124 at the receiver end 126 is greater than the outer diameter of the shaft 124 at the emitter end 128. The flange 104 can be configured with faces that are straight, conical, or curved. A shape of the flange 104 can be curved, such as the cup-like shape shown in the example of FIG. 3A. An inner concave surface of the flange 104 can be configured to accommodate the foam body 106A, and an external surface of flange 104 can be configured to engage the ear canal.

Figure 3B:
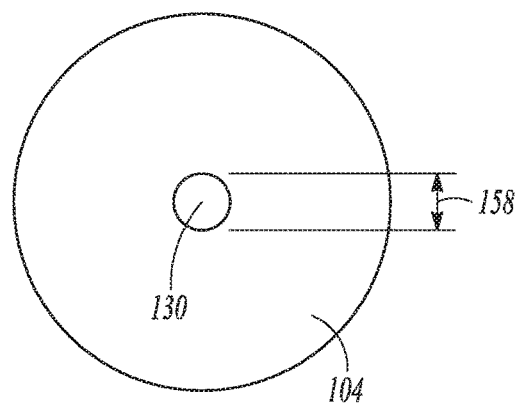
FIG. 3B includes an end view of an example of a portion of an earplug.

FIG. 3B includes an end view of an example of a portion of the earplug 102. The bore 130 has a bore diameter 158.

Figure 4:
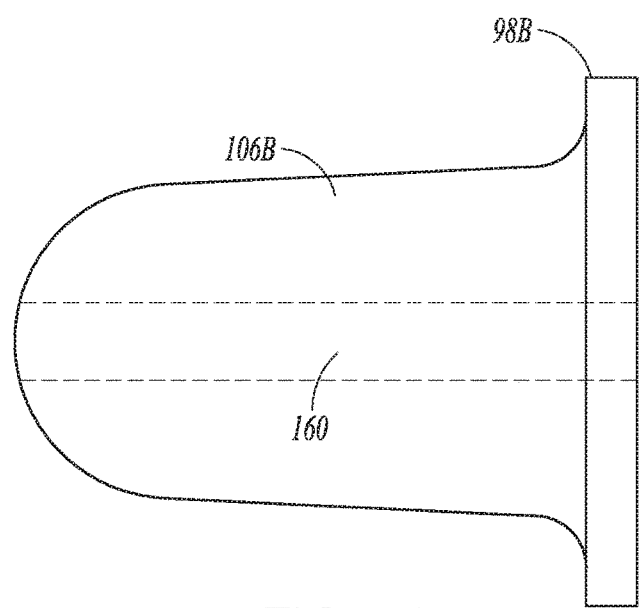
FIG. 4 illustrates an example of a foam body.

FIG. 4 illustrates an example of the foam body 106B. The foam body 106B has a channel 160 extending through its center as shown in the example of FIG. 4. The shaft 124 extends into the channel 160. A diameter of the channel 160 corresponds to an outer diameter of the shaft. In one example, the diameter of the channel 160 is less than the outer diameter of the shaft, such that the channel 160 is expanded from its resting state. In another example, the diameter of the channel 160 can be the same as or larger than the outer diameter of the shaft. In one example, the foam body 106B comprises memory foam such as polyurethane (PU). In various examples, foam body 106B is fabricated of polyvinyl chloride (PVC) or phthalate-free vinyl.

A shape of the foam body 106B has a larger outer diameter at one end, as shown in FIG. 4. The size and shape of the foam body 106B is configured to fit inside the ear canal. The foam body 106B can have a compressed state or an expanded state. The foam body 106B can become compressed when the user presses the foam body 106B between two fingers, for example. The foam body 106B expands from the compressed state and returns to a natural configuration when the external compression is removed.

In FIG. 4, flange 98B is squared at both the inner edge and at the outer edge. Flange 98B can aid in device retention. In some examples, flange 98B can be positioned behind the tragus.

The foam body 106B abuts the inner concave surface of the flange 104, such as shown in the example of FIG. 1A. The user can compress the foam body 106B for insertion into the ear canal. In the compressed state, the foam body 106B allows for easier insertion. The first end of the earplug 102 is inserted into the ear canal. The earplug 102 is placed at a desired position in the ear canal. The flange 104 is configured to anchor (e.g., hold in place) the earplug 102. The foam body 106B can expand from the compressed state to engage the ear canal. The flange 104 anchors the earplug 102 in place by engaging the ear canal. The flange 104 has an outer surface (e.g., opposite the inner concave surface). The outer surface of the flange 104 presses against the ear canal having a diameter less than a flange diameter. One or more seals can be created in the ear canal. A seal can be created by a component of the earplug 102 engaging (e.g., pressing against, held in place by friction, or touching) the ear canal.

The flange 104 engages the ear canal, and creates a first flange seal in the ear canal. The first flange seal anchors the earplug in place during insertion, and attenuates sound. A potential advantage of the present subject matter can include that the user may not need to hold the earplug in place while waiting for the foam body 106B to expand. Flange 104, in one example, is self-centering in the ear canal and compressive forces exerted by the foam body are sufficient to maintain an open path for audio frequency vibrations notwithstanding contortions of the path of shaft 124.

The foam body 106B can expand to a size and shape of the ear canal. As such, an outer surface of the foam body 106B engages the ear canal. The foam body 106B creates a foam body seal. The foam body seal can aid in anchoring the earplug in place during use, and can attenuate sound. The user can wear the earplug 102 for long periods of time (e.g., an hour, multiple hours, or for a day), without removing the earplug 102 from the ear.

In an example, the outer diameter of the shaft can be different at the receiver end 126 and the emitter end 128 due to the taper of the shaft 124. In an example, the shaft 124 is configured to passively push (e.g., due to the taper) the foam body 106B toward the first end 108. The foam body 106B is passively pushed toward the flange 104. This enhances the first flange seal by encouraging the flange 104 to press into (e.g., expand into) the ear canal.

The first durometer allows the shaft 124 to bend to conform to a non-uniform shape of the ear canal. The foam body 106B is configured to support the shaft 124, such as to prevent the bore 130 from collapsing. As such, the foam body 106B can aid in preventing a blockage of sound through bore 130.

Figure 5A:
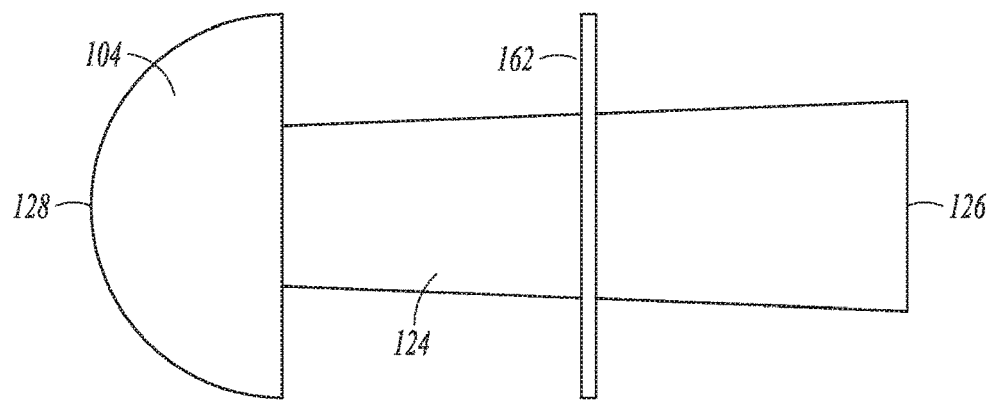
FIGS. 5A, 5B, and 5C illustrate a portion of an earplug, according to some examples.

FIG. 5A illustrates a portion of the earplug 102, according to an example. The flange 104 is coupled to the shaft 124. In one example, the flange 104 and the shaft 124 are molded out of the same material as single piece. The earplug 102 includes a member configured to position the foam body at a desired location along the shaft 124. In an example, the member is a secondary flange 162. In other examples, the member is a stud, a pin, or other protrusion.

FIG. 5A is a side view of the shaft. In an end view, the secondary flange 162 has a circular shape. The secondary flange 162 is fixed at an axial position on the shaft 124. In one example, secondary flange 162 is affixed along a length of shaft 124 and in other examples, secondary flange 162 is affixed at or near an end of the length of shaft 124 (receiver end 126).

In an example, the foam body 106B (not shown in this view) is positioned between the secondary flange 162 and the base plate 118 (not shown in this view). When the earplug 102 is in the ear canal, the resulting space (e.g., air gap, air, opening, or recess) between the flange 104 located at the emitting end 128 and the foam body 106B can aid in reducing the sound reaching the eardrum.

In an example, a portion of the flange 104 (e.g., the portion of the flange 104 between the secondary flange 162 and emitter end 128 in the example of FIG. 5A) is configured to conform to a shape of the ear canal. The shape of the ear canal can bend or can narrow. As such, the portion of the flange 104 is configured to be flexible to fit into the shape of the ear canal.

In an example, the ear canal can have an oblong narrowing portion. The flange 104 can be configured to aid in centering the emitter end 128 in the ear canal, such as to aid in sound blockage.

Figure 5B:
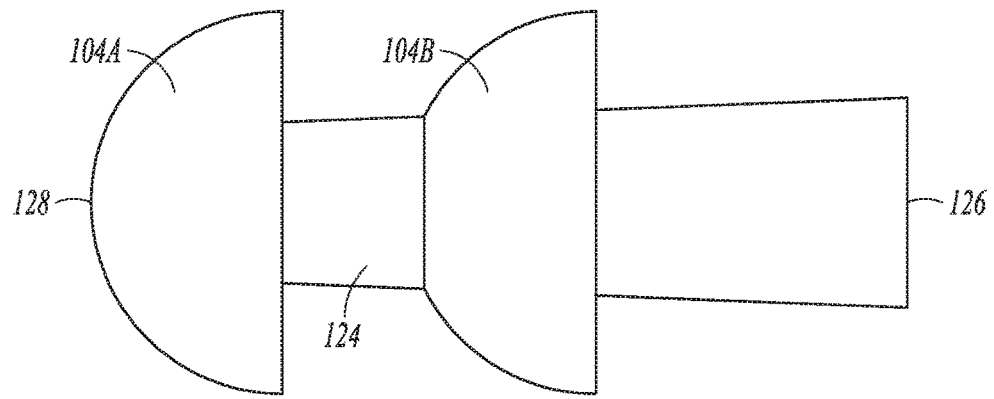

FIG. 5B illustrates a portion of the earplug 102, according to an example. In one example, the earplug 102 includes multiple flanges, such as an end-flange 104A and a middle-flange 104B. The middle-flange 104B is positioned between the receiver end 126 and the emitter end 128. The end-flange 104A is positioned at the emitter end 128. The end-flange 104A and the middle-flange 104B are configured to create a seal in the ear canal. The end-flange 104A has the same or similar shape as the middle-flange 104B. In another example, end-flange 104A has a shape or size different than the middle-flange 104B.

In one example, the earplug 102 can include an arrangement along the shaft 124 including the foam body 106B (not shown) between the end-flange 104A and the middle-flange 104B.

Figure 5C:
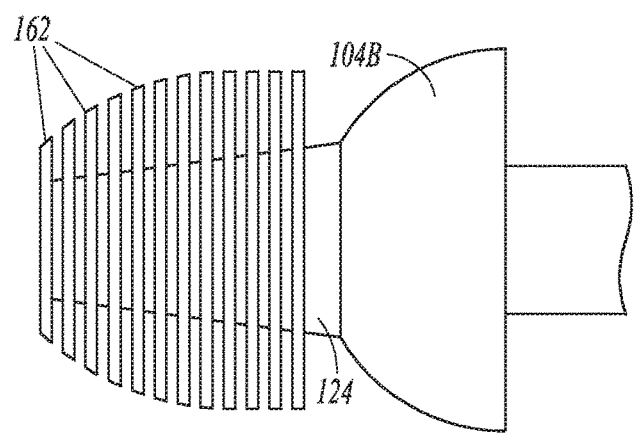

FIG. 5C illustrates a portion of the earplug 102, according to an example. The secondary flange 162 is positioned at a desired location along the length of the shaft 124. In an example, the earplug 102 can include multiple secondary flanges 162, such as illustrated in FIG. 5C. The multiple secondary flanges 162 can have varying shapes along the length of the shaft 124. In an example, each of the multiple secondary flanges 162 creates a seal in the ear canal. In an example, a space can be between each of the multiple secondary flanges 162. In an example, the multiple secondary flanges 162 can be molded with the shaft 124 as a single piece, such as shown in FIG. 5C.

In another example, the multiple secondary flanges 162 can be separate pieces from the shaft 124. The multiple secondary flanges 162 can include a circular opening. In this example, the multiple secondary flanges 162 can be coupled to the shaft 124. The multiple secondary flanges 162 can be positioned on the shaft 124 using the circular opening. The multiple secondary flanges 162 can be stacked, such as to provide an arrangement like that of the example of FIG. 5C. The multiple secondary flanges 162 are stacked by placing a secondary flange on top of another with a spacer member in between.

In an example, the foam body 106B is made of a single piece of foam. Or, for example, the foam body 106B can be comprised out of multiple pieces of foam, such that there are multiple foam members positioned along the length of the shaft 124. In one example, the multiple foam members can be positioned next to one another. In an example, the multiple foam members can be separated, such as by the middle-flange 104B or the secondary flange 162. In an example, the foam body 106B is replaceable, such that the user can select a different foam body 106B for different uses of the earplug 102.

Figure 6:
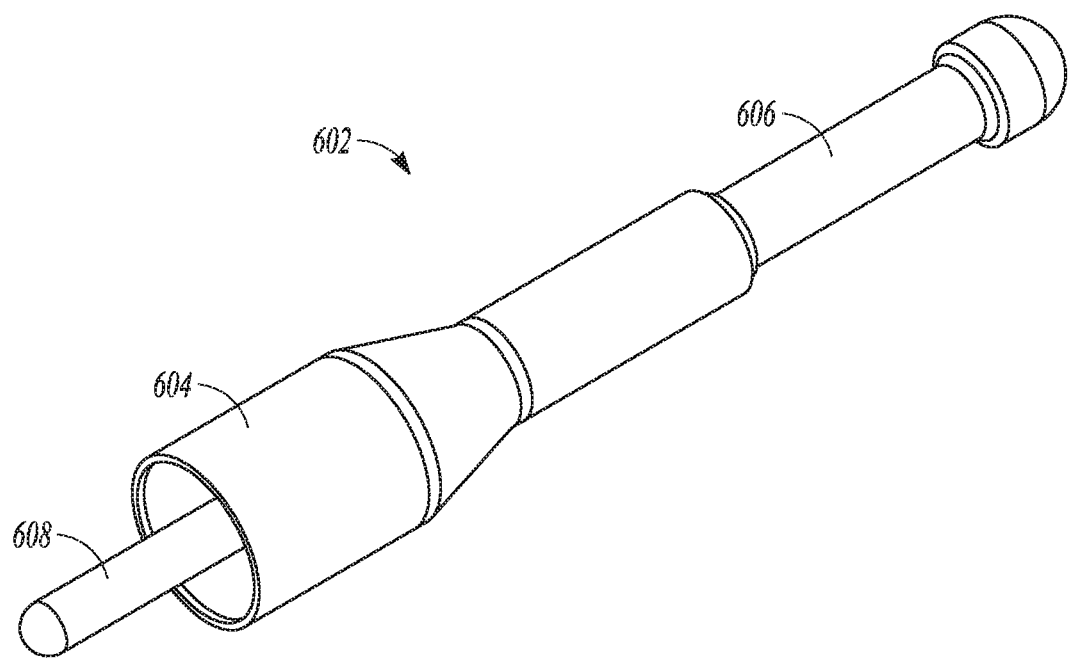
FIG. 6 illustrates an example of a tool.

FIG. 6 illustrates an example of a tool 602. The tool 602 includes a flange-compression member 604, a handle 606, and a bore-pin 608. The handle 606 is coupled to the flange-compression member 604. The bore-pin 608 is coupled to the handle 606. The bore-pin 608 is positioned at least partially inside of the flange-compression member 604, as illustrated in FIG. 6. The tool 602 has a metal material. A size of the bore-pin 608 corresponds to the bore 130. A size of the flange-compression member 604 corresponds to the flange 104. A diameter of the flange-compression member 604 is less than a diameter of the flange 104. In one example, bore-pin 608 is omitted and a flanged structure can be folded into cylinders to allow for replacement or customization. In one example foam body 106B can be replaced from the filter end using tool 602.

Tool 602 can be provided as a component of a kit including various size foam body elements, shafts, filters and other components. A kit can allow a user to customize an ear plug to accommodate a wide variety of ear canal sizes, shapes, and suited for a specific sound environment.

In an example, the tool 602 has a plastic material (e.g., the second material).

Figure 7:
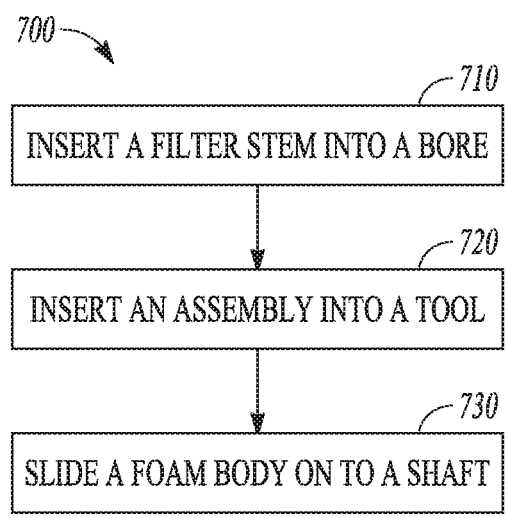
FIG. 7 illustrates an assembly method, according to an example.

FIG. 7 illustrates an assembly method 700, according to an example. At 710, the filter stem 132 is inserted into the bore 130.

At 720, an assembly is inserted onto the tool 602. The assembly includes a first portion that can include the shaft 124 and the flange 104, and a second portion that can include the filter stem 132 and the cap 110A. The emitter end 128 of the shaft 124 is slid onto the bore-pin 608, and the flange 104 is compressed into the flange-compression member 604. The bore-pin 608 is positioned inside the bore 130. The bore-pin 608 is configured to support the shaft 124.

At 730, the foam body 106B is slid onto the shaft 124. For example, the foam body 106B is inserted onto the handle 606, such that the handle 606 is inside of the channel 160. The foam body 106B is pushed over the flange-compression member 604, and then the foam body 106B is pushed onto the shaft 124. The assembly is removed from the tool 602.

NOTES & EXAMPLES

The sound attenuation system can include one or more components, such as the earplug 102 or a pair of earplugs coupled to each other by a cord.

In an example, the flange 104 is a separate piece from the shaft 124.

In an example, the cap 110A can be coupled to the base plate 118 using one or more connecters. In an example, the connecter can include a plastic member having a spring constant. In an example, the earplug 102 can include two or more plastic members positioned along a circumference of the cap 110A. The plastic member can be configured such that the cap 110A is substantially parallel to the base plate 118 in the first position and in the second position. In this example, the space 172 is a space between the port boss 114 and the cavity 138 in the second position. The cap 110A can be pushed onto the port boss 114, to configure the cap in the first position. There can be a friction connection between the cavity 138 and the port boss 114 in the first position. The friction connection can oppose the force of the plastic member having the spring constant, such as to retain the cap 110A in the first position. The user can move the cap 110A to the second position, such as by overcoming the friction connection.

In an example, the connector can include a cord.

In an example, the cap 110A is removable from the earplug 102.

Figure 8:
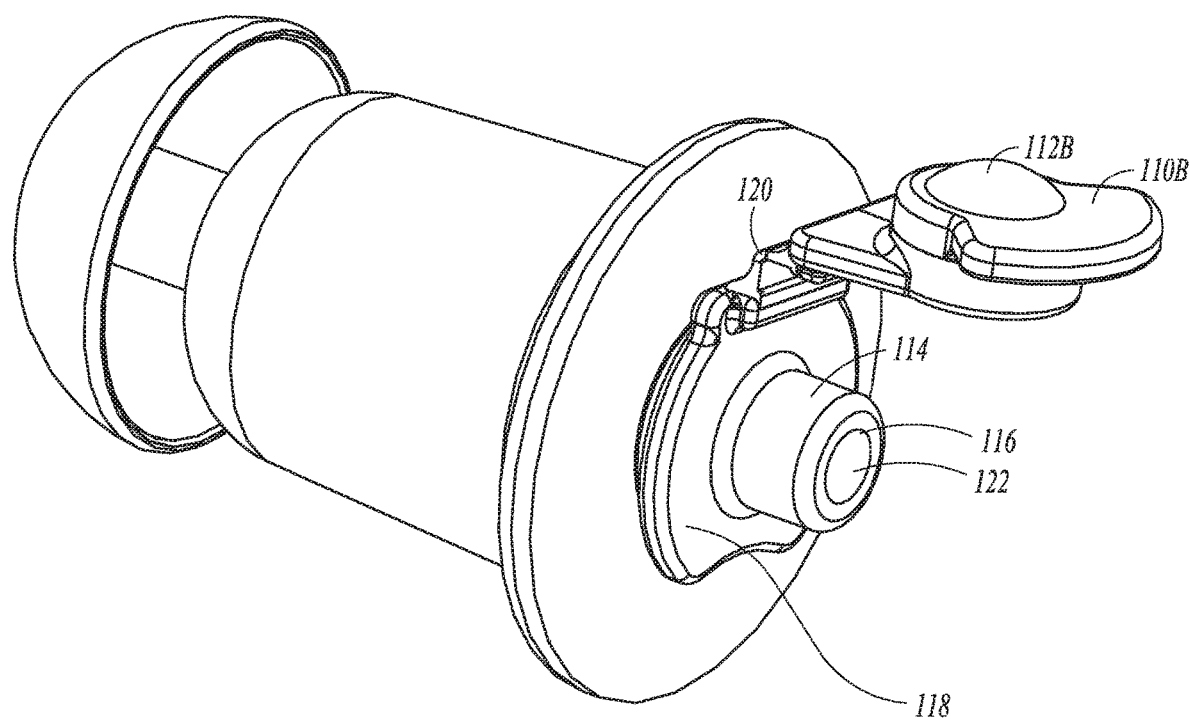
FIG. 8 illustrates an example of a sound filter.

FIG. 8 illustrates an example of a sound filter. In the example illustrated, joint 120 is coupled to cap 110B and coupled to knob 112B. Cap 110B, in the example shown has an offset portion. The offset portion provides a gap between base plate 118 and cap 110B to facilitate manipulation by a user.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. Some examples include the following.

Example 1 can include or use subject matter (such as an apparatus, a method, or a means for performing acts) such as can include or use a sound attenuation system comprising a first end including a shaft and a flange. The flange is coupled to the shaft. The shaft has a first durometer. The shaft having a bore between a receiver end and an emitter end. The system comprising a second end including a filter stem coupled to a cap by a joint. The filter stem has a second durometer. The filter stem has a hole between an inlet end and an outlet end. The filter stem has a port boss. The outlet end is coupled to the receiver end. The cap includes a cavity having a cavity diameter that corresponds to an outer diameter of the port boss. The joint is configured to allow the cap to have a first position in which the cap occludes the hole and to have a second position in which the cap is clear of the hole.

Example 2 can include, or can optionally be combined with the subject matter of Example 1, to optionally include a foam body having a channel, the shaft extending into the channel.

Example 3 can include, or can optionally be combined with the subject matter of any one of Examples 1 or 2 wherein an outer diameter of the shaft is tapered.

Example 4 can include, or can optionally be combined with the subject matter of any one of Examples 1-3, wherein the outer diameter of the shaft at the receiver end is greater than the outer diameter of the shaft at the emitter end.

Example 5 can include, or can optionally be combined with the subject matter of any one of Examples 1-4, further comprising a base plate coupled to the filter stem.

Example 6 can include, or can optionally be combined with the subject matter of any one of Examples 1-5, wherein the joint is coupled to the base plate.

Example 7 can include, or can optionally be combined with the subject matter of any one of Examples 1-6, further comprising a gap between the base plate and the cap when in the first position.

Example 8 can include, or can optionally be combined with the subject matter of any one of Examples 1-7, further comprising a secondary flange coupled to the shaft.

Example 9 can include, or can optionally be combined with the subject matter of any one of Examples 1-8, wherein the filter stem is at least partially inside of the bore.

Example 10 can include, or can optionally be combined with the subject matter of any one of Examples 1-9, wherein the flange is curved.

Example 11 can include, or can optionally be combined with the subject matter of any one of Examples 1-10, further comprising a foam body having a channel, the shaft extending into the channel.

Example 12 can include, or can optionally be combined with the subject matter of any one of Examples 1-11, wherein the foam body abuts a concave portion of the flange.

Example 13 can include, or can optionally be combined with the subject matter of any one of Examples 1-12, wherein a diameter of the channel corresponds to an outer diameter of the shaft.

Example 14 can include or use subject matter (such as an apparatus, a method, or a means for performing acts), such as can include or use a sound filter for an earplug, the sound filter comprising a filter stem coupled to a cap by a joint. The filter stem has a hole between an inlet end and an outlet end. The filter stem has a port boss. The joint is configured to allow the cap to have a first position in which the cap occludes the hole and to have a second position in which the cap is clear of the hole.

Example 15 can include, or can optionally be combined with the subject matter of Example 14, wherein the cap includes a cavity having a cavity diameter that corresponds to an outer diameter of the port boss.

Example 16 can include, or can optionally be combined with the subject matter of any one of Examples 14 or 15, wherein a portion of the filter stem is tapered.

Example 17 can include, or can optionally be combined with the subject matter of any one of Examples 14-16, wherein the hole includes a first chamber having a first diameter and a second chamber having a second diameter.

Example 18 can include, or can optionally be combined with the subject matter of any one of Examples 14-17, wherein the hole includes a third chamber having a third diameter.

Example 19 can include, or can optionally be combined with the subject matter of any one of Examples 14-18, wherein the first diameter is less than the second diameter.

Example 20 can include, or can optionally be combined with the subject matter of any one of Examples 14-19, further comprising a knob coupled to the cap, the knob on an opposite side of the cap as the cavity.

Example 21 can include, or can optionally be combined with the subject matter of any one of Examples 14-20, further comprising a base plate coupled to the filter stem, a gap between the base plate and the cap, wherein the joint is coupled to the base plate and wherein the gap is present in the first position.

Example 22 can include, or can optionally be combined with the subject matter of any one of Examples 14-21, wherein the base plate includes a notch.

Example 23 can include or use subject matter (such as an apparatus, a method, or a means for performing acts), such as can include or use a sound attenuation system comprising a foam body having an inner channel extending between a receiver end and an emitter end. The body has a cylindrical portion coaxial with the channel. The body includes an elastic foam configured to return to a natural configuration after an external compressive force is applied and removed. The system includes a shaft configured for placement within the channel between the receiver end and the emitter end. The shaft includes an inner bore aligned axially and includes a flange affixed proximate the emitter end, and wherein the shaft is configured to maintain a configuration determined by the foam body and wherein the inner bore remains open.

Example 24 can include, or can optionally be combined with the subject matter of Example 23, wherein the foam body includes polyvinyl chloride or polyurethane.

Example 25 can include, or can optionally be combined with the subject matter of any one of Examples 23 or 24, wherein the foam body has a flange at the receiver end.

Example 26 can include, or can optionally be combined with the subject matter of any one of Examples 23-25, wherein the shaft includes silicone.

Example 27 can include, or can optionally be combined with the subject matter of any one of Examples 23-26, wherein the flange is curved.

Example 28 can include, or can optionally be combined with the subject matter of any one of Examples 23-27, further comprising a filter coupled to engage with the bore, the filter having an axial lumen configured to convey audio frequency vibrations.

Example 29 can include, or can optionally be combined with the subject matter of any one of Examples 23-28, wherein the axial lumen includes an orifice.

Example 30 can include, or can optionally be combined with the subject matter of any one of Examples 23-29, wherein the axial lumen includes at least two chambers.

Example 31 can include, or can optionally be combined with the subject matter of any one of Examples 23-30, further including a base plate coupled to a receiver end of the filter.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A sound attenuation system comprising:
   a first end including a shaft and a flange, the flange coupled to the shaft, the shaft having a first durometer, and the shaft having a bore between a receiver end and an emitter end;
   a second end including a filter stem coupled to a cap by a joint, the filter stem having a second durometer, the filter stem having a hole between an inlet end and an outlet end, the filter stem having a port boss;
   wherein the outlet end is configured to be inserted into the bore of the shaft at the receiver end; and
   wherein the cap includes a cavity having a cavity diameter that corresponds to an outer diameter of the port boss and wherein the joint is configured to allow the cap to have a first position in which the cap occludes the hole and to have a second position in which the cap is clear of the hole.

2. The sound attenuation system of claim 1, further comprising:
   a foam body having an inner channel, the body having a cylindrical portion coaxial with the inner channel, the body including an elastic foam configured to return to a natural configuration after an external compressive force is applied and removed,
   wherein the shaft is configured for placement within the inner channel of the foam body, and
   wherein the foam body includes polyvinyl chloride or polyurethane.

3. The sound attenuation system of claim 1, further comprising:
   a foam body having an inner channel, the body having a cylindrical portion coaxial with the inner channel, the body including an elastic foam configured to return to a natural configuration after an external compressive force is applied and removed,
   wherein the shaft is configured for placement within the inner channel of the foam body, and
   wherein the foam body has a foam-body flange at the receiver end.

4. The sound attenuation system of claim 1, wherein the shaft includes silicone.

5. The sound attenuation system of claim 1, wherein the flange is curved.

6. The sound attenuation system of claim 1, further comprising a filter coupled to engage with the bore, the filter having an axial lumen configured to convey audio frequency vibrations.

7. The sound attenuation system of claim 6, wherein the axial lumen includes an orifice.

8. The sound attenuation system of claim 6, wherein the axial lumen includes at least two chambers.

9. The sound attenuation system of claim 1, wherein the flange has a planar shape.

10. The sound attenuation system of claim 1, wherein the flange has a longitudinal cross-sectional shape that includes a convex curved face.

11. The sound attenuation system of claim 1, wherein the flange has a cross-sectional shape that includes a conical face.

12. The sound attenuation system of claim 1, further comprising:
    a foam body having an inner channel, the body having a cylindrical portion coaxial with the inner channel, the body including an elastic foam configured to return to a natural configuration after an external compressive force is applied and removed,
    wherein the shaft is configured for placement within the inner channel of the foam body, and
    wherein the foam body is made from a single piece of foam.

13. The sound attenuation system of claim 1, further comprising an attachment, wherein the attachment is configured to connect to the port boss.

14. The sound attenuation system of claim 1, further comprising an attachment, wherein the attachment is configured to connect to the port boss, and wherein the attachment includes a hearing aid.

15. The sound attenuation system of claim 1, further comprising an attachment, wherein the attachment is configured to connect to the port boss, and wherein the attachment is a telecommunications device.

16. The sound attenuation system of claim 1, further comprising an attachment, wherein the attachment is configured to connect to the port boss, and wherein the attachment is a headset.

17. The sound attenuation system of claim 1, wherein the port boss includes a raised ring spaced from the inlet end and configured to aid in securing an interference-fit coupling to an attachment that fits over the port boss.

18. The sound attenuation system of claim 1, wherein the positioning flange is coupled to the shaft nearer the receiving end of the shaft than the emitting end of the shaft.

19. The sound attenuation system of claim 1, further comprising:
    a foam-body-replacement tool, wherein the tool includes:
       a handle;
       a flange-compression member coupled to the handle; and
       a bore-pin coupled to the handle, wherein the bore pin is positioned at least partially inside of the flange-compression member, wherein a size of the bore pin corresponds to a size of the bore of the shaft, and wherein a size of the flange-compression member corresponds to the flange.

20. The sound attenuation system of claim 1, further including:
   a plurality of foam body elements of various sizes configured to be alternatively placed on the shaft to customize an ear plug to accommodate different ear-canal sizes and shapes; and
   a foam-body-replacement tool, wherein the tool includes:
      a handle;
      a flange-compression member coupled to the handle;
      a bore-pin coupled to the handle, wherein the bore pin is positioned at least partially inside of the flange-compression member, wherein a size of the bore pin corresponds to a size of the bore of the shaft, and wherein a size of the flange-compression member corresponds to the flange.

21. The sound attenuation system of claim 1, further including:
   a plurality of alternative various size foam body elements configured to be alternatively placed on the shaft to customize an ear plug that includes the shaft and one of the plurality of alternative various size foam body elements to accommodate different ear-canal sizes and shapes; and
   a foam-body-replacement tool, wherein the tool includes:
      a handle;
      a flange-compression member coupled to the handle;
      a bore-pin coupled to the handle, wherein the bore pin is positioned at least partially inside of the flange-compression member, wherein a size of the bore pin corresponds to a size of the bore of the shaft, and wherein a size of the flange-compression member corresponds to the flange.

22. The sound attenuation system of claim 1, further including:
   a foam body having an inner channel, the body having a cylindrical portion coaxial with the inner channel, the body including an elastic foam configured to return to a natural configuration after an external compressive force is applied and removed, wherein the shaft is configured for placement within the inner channel of the foam body;
   at least one alternative shaft configured to be alternatively placed in the foam body to customize an ear plug that includes the at least one alternative shaft placed in the foam body; and
   a foam-body-replacement tool, wherein the tool includes:
      a handle;
      a flange-compression member coupled to the handle;
      a bore-pin coupled to the handle, wherein the bore pin is positioned at least partially inside of the flange-compression member, wherein a size of the bore pin corresponds to a size of the bore of the shaft, and wherein a size of the flange-compression member corresponds to the flange.

23. The sound attenuation system of claim 1, wherein the flange is molded with the shaft as a single piece of material.

24. The sound attenuation system of claim 1, wherein the flange is one of a plurality of flanges coupled to the shaft nearer the emitter end of the shaft than the receiver end of the shaft, wherein the plurality of flanges is stacked together such that each one of the plurality of flanges is separated from adjacent flanges of the plurality of flanges by a space.

* * * * *